US009220783B2

(12) United States Patent
 Taylor

(10) Patent No.: US 9,220,783 B2
(45) Date of Patent: *Dec. 29, 2015

(54) THERAPEUTIC COMPOSITION WITH A BOTULINUM NEUROTOXIN

(71) Applicant: MERZ PHARMA GmbH & CO. KGaA, Frankfurt am Main (DE)

(72) Inventor: Harold Victor Taylor, Frankfurt am Main (DE)

(73) Assignee: MERZ PHARMA GmbH & CO. KGaA, Frankfurt am Main (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/704,320

(22) Filed: May 5, 2015

(65) Prior Publication Data

US 2015/0231259 A1    Aug. 20, 2015

Related U.S. Application Data

(60) Continuation of application No. 14/134,505, filed on Dec. 19, 2013, which is a continuation of application No. 13/738,283, filed on Jan. 10, 2013, now Pat. No. 8,652,489, which is a continuation of application No. 12/928,898, filed on Dec. 22, 2010, now Pat. No. 8,372,645, which is a division of application No. 11/184,495, filed on Jul. 19, 2005, now Pat. No. 7,879,341.

(60) Provisional application No. 60/591,196, filed on Jul. 26, 2004.

(51) Int. Cl.

| A61K 38/48 | (2006.01) |
|---|---|
| A61K 39/00 | (2006.01) |
| C07K 14/33 | (2006.01) |
| A61K 47/36 | (2006.01) |
| A61K 47/26 | (2006.01) |
| A61K 47/32 | (2006.01) |
| A61K 9/19 | (2006.01) |
| A61K 47/10 | (2006.01) |

(52) U.S. Cl.
CPC . *A61K 47/36* (2013.01); *A61K 9/19* (2013.01); *A61K 38/4893* (2013.01); *A61K 47/10* (2013.01); *A61K 47/26* (2013.01); *A61K 47/32* (2013.01); *C12Y 304/24069* (2013.01)

(58) Field of Classification Search
None
See application file for complete search history.

(56) References Cited

U.S. PATENT DOCUMENTS

| 5,215,743 | A | 6/1993 | Singh et al. |
|---|---|---|---|
| 5,512,547 | A | 4/1996 | Johnson et al. |
| 5,756,468 | A | 5/1998 | Johnson et al. |
| 7,879,341 | B2 | 2/2011 | Taylor ..................... 424/247.1 |
| 7,964,199 | B1 | 6/2011 | Bigalke |
| 8,372,645 | B2 | 2/2013 | Taylor ............................ 436/8 |
| 8,652,489 | B2 | 2/2014 | Taylor ..................... 424/247.1 |
| 8,841,080 | B2 | 9/2014 | Taylor et al. .................. 435/7.2 |
| 9,050,367 | B2 * | 6/2015 | Taylor ................................. 1/1 |
| 2002/0058624 | A1 | 5/2002 | Hanyu et al. |
| 2003/0118598 | A1 | 6/2003 | Hunt |
| 2003/0138437 | A1 | 7/2003 | Hunt |
| 2004/0009180 | A1 | 1/2004 | Donovan |
| 2004/0033241 | A1 | 2/2004 | Donovan |
| 2004/0151741 | A1 | 8/2004 | Borodic |
| 2005/0234012 | A1 | 10/2005 | Jafari |
| 2005/0238720 | A1 | 10/2005 | Vukmirovic et al. |
| 2012/0201857 | A1 | 8/2012 | Modi ........................... 424/400 |
| 2013/0121987 | A1 | 5/2013 | Taylor ....................... 424/94.67 |
| 2013/0224248 | A1 | 8/2013 | Taylor et al. ............... 424/239.1 |
| 2014/0105882 | A1 | 4/2014 | Taylor ......................... 424/94.3 |

FOREIGN PATENT DOCUMENTS

| EP | 0 211 592 | 2/1987 |
|---|---|---|
| EP | 0 351 162 | 1/1990 |
| JP | 62-36332 | 2/1987 |
| JP | 03004791 | 1/1991 |
| JP | 3 504721 | 10/1991 |
| JP | 2002 187852 | 5/2002 |
| WO | WO 97/27841 | 8/1997 |
| WO | WO 00/15245 | 3/2000 |
| WO | WO 00/74703 | 12/2000 |
| WO | WO 01/58472 | 8/2001 |
| WO | WO 2004/060384 A1 | 7/2004 |

OTHER PUBLICATIONS

Muldrew, K. "Cryoprotective Compounds" University of Calgary, published Nov. 24, 1998.
Dasgupta, et al., Journal of Biological Chemistry, 1967, 243 (5):1065 (Abstract)
Chen, et al., Infect Immun. 1998, 66:2420-5. (Abstract).
EMEA, Anexo I, http://www.emea.europa.eu/pdfs/human/referral/botox/426003es.pdf, 2003, pp. 1-21.

(Continued)

*Primary Examiner* — Nita M Minnifield
(74) *Attorney, Agent, or Firm* — Hueschen and Sage

(57) ABSTRACT

The present invention pertains to pharmaceutical compositions which comprise a botulinum neurotoxin from *Clostridium botulinum*, the neurotoxin being free of the complexing proteins naturally present in the botulinum neurotoxin complex or being chemically modified or being modified by genetic manipulation. Moreover the pharmaceutical compositions of the instant invention have good stability and are advantageously formulated free of human serum albumin.

6 Claims, No Drawings

(56) References Cited

OTHER PUBLICATIONS

EMEA, Annex I (English translation) http://www.emea.europa.eu/pdfs/human/referral/botox/426003es.pdf, 2003, pp. 1-21.
Dolly, J. Oliver, Mecanismo de acción de la meurotoxina botulinica, http://www.neurotoxininstitute.com/es/chapter_moa.asp, 2005, pp. 1-14.
Dolly, J. Oliver, (English translation) Botulinum Neurotoxin Mechanism of Action, http://www.neurotoxininstitute.com/es/chapter_moa.asp, 2005, pp. 1-14.
Infodoctor, http://www.infodoctor.org/www/meshd.htm?idos=29455, 2007, pp. 1-3.
Infodoctor, (English translation) http://www.infodoctor.org/www/meshd.htm?idos=29455, 2007, pp. 1-3.
E-move (MD Virtual University, Jul. 5, 2004). (Abstract only).
Carruthers, et al. (Dermatologic Surgery, Aug. 2003, vol. 29 No. 8, pp. 802-809) (Abstract only).
Schantz, et al. (Journal of the Association of Official Analytical Chemists, 1978, vol. 61, No. 1, pp. 96-99) (Abstract only).
Singh, et al. (AAPS PharmSci Tech, 2003 vol. 4, No. 3, pp. E42) (Abstract only).
Goodman, G. Dermatologic Surgery (2003) pp. 533-538, vol. 29.
International Search Report, eight (8) pages, Mar. 3, 2006.
Written Opinion, twelve (12) pages, Mar. 3, 2006.
Botox® Cosmetic Product Literature.
Malizio, et al. Methods in Molecular Biology, 2000, 145:27-39.
Randolph, Journal of Pharmaceutical Sciences, 1997, 86:1198-1203.
Anchordoquy, et al. Archives of Biochemistry and Biophysics, 1996, 332:231-238.
Miekka, et al. Vox Sanguinis, 1975, 29:101-123.

\* cited by examiner

THERAPEUTIC COMPOSITION WITH A BOTULINUM NEUROTOXIN

The present invention pertains to pharmaceutical compositions which comprise a botulinum neurotoxin from *Clostridium botulinum*, the neurotoxin being free of the complexing proteins naturally present in the botulinum neurotoxin complex, or a botulinum neurotoxin which is modified chemically or modified by genetic manipulation said modified botulinum toxin being free of the complexing proteins which naturally form complexes with botulinum neurotoxins. Moreover the pharmaceutical compositions of the instant invention have good stability and are advantageously formulated free of human serum albumin.

Albumin of human origin has been utilized as a bulk carrier and stabilizer for protein active ingredients present in pharmaceutical compositions. Albumin has been demonstrated to stabilize proteinaceous active ingredients in pharmaceutical compositions by reducing adhesion and reducing denaturation of the active ingredient. Moreover, the albumin has no immunogenicity on injection into a human patient.

Significant drawbacks exist, however, to the use of albumin in a pharmaceutical composition. Albumin has been attributed to transmission of certain stable viruses, prions or other infectious or pathogenic compounds, e.g., human transmissible spongiform encephalopathy (TSE). Consequently, there is increased regulatory scrutiny of pharmaceutical compositions containing human serum albumin. Similarly, gelatin has been used in some pharmaceutical compositions containing protein active ingredients as an albumin substitute. As a mammalian derived protein, gelatin also poses the same risk of pathogen transmission. Therefore, there is a need for a replacement for mammalian derived proteinaceous stabilizers.

Botulinum toxin complexes are composed of a mixture of clostridial proteins. These are hemagglutinins with different molecular masses, a nontoxic, non-hemagglutinating protein (Mr about 120,000) and a neurotoxin (Mr about 150,000). They form an acid-stable complex which is responsible for the oral toxicity in cases of food poisoning. In contrast to the pure neurotoxin, the complex resists the aggressive environment in the gastrointestinal tract and makes enteral absorption of the neurotoxin possible, and this reaches the target cells via the bloodstream or the lymphatic system and there induces blockade of neurotransmitter release. This is followed by muscle paralysis and cessation of various autonomic functions. Poisoned patients die of respiratory muscle failure. Since the pure neurotoxin is degraded in the gastrointestinal tract and thus does not undergo enteral absorption, it is not toxic after ingestion. On parenteral administration, the therapeutic effects of the neurotoxin and of the complex do not differ since the complex decomposes into its constituents in tissue, and only the neurotoxin is taken up by the target cells.

At present two products comprising botulinum neurotoxin type A are approved for the treatment of blepharospasm, hemifacial spasms and spasmodic torticollis: BOTOX® and DYSPORT®. The botulinum neurotoxin is in the current state of the art injected directly into dystonic or spastic muscles, where the neurotoxin is released at physiological pH from the complex and elicits the desired pharmacological effect. Clinical trials for treating other disorders of the nervous system (e.g. spasticities, migraine, low back pain, cervical spine disorders, hypersalivation) are currently in progress. Botulinum toxin complex type A (Mr 900,000) is approved for the therapy of various dystonias. The approved products are also employed for cosmetic indications such as hyperhidrosis and pronounced wrinkling. The other *Clostridium botulinum* toxin complexes (of types B, C1, D, E, F, G) as well as toxins which are derived from these *Clostridium botulinum* toxins by chemical modification or genetic manipulation are also suitable for these therapies.

Both BOTOX® and DYSPORT® are provided to clinicians in lyophilized form for reconstitution just prior to use. Unfortunately, not every patient and indication requires the same dosage. Consequently, reconstituted composition is often either frozen or refrigerated for later use. These held over reconstituted compositions have been evaluated for potency stability. It has been observed that BOTOX® looses at least 44% of its potency when it is reconstituted and stored under refrigeration for 12 hours. Moreover, when the reconstituted composition is frozen at −70° C., it loses 70% of its potency. Gartlan, M. G., and Hoffman, H. T. Crystalline preparation of botulinum toxin type A (Botox): Degradation in potency with storage, Otolaryngology—Head and Neck Surgery 102(2): 135-140 (1992). Such instability results in significant dosage variation and wasted product. Thus, an object of the instant invention is the development and production of a stable liquid and freeze-dried formulation of botulinum toxin which has better handling characteristics than existing formulations.

A novel pharmaceutical composition has been developed which comprises botulinum neurotoxin (type A, B, C1, D, E, F, or G) which is free of hemagglutinins and other exogenous proteins. This reduces the total protein load of a pharmaceutical formulation without reduction of the amount of toxin. We found in antigenicity studies that the pure neurotoxin of all types, in contrast to commercial products of type A and the complexes of types B to G, induces no, or at the most very little, formation of antibodies. On therapeutic use of this newly developed pharmaceutical (pure neurotoxin of types A, B, C1, D, E, F, or G), there is no failure of therapy due to antibodies even after repeated administration.

However, and as noted above, problems arise on formulation. As a proteinaceous active, botulinum toxin is very labile. Furthermore, botulinum toxin complexes are extremely susceptible to denaturation due to surface denaturation, heat, and alkaline conditions.

As with enzymes generally, the biological activities of botulinum toxins (which are intracellular peptidases) is dependant, at least in part, upon their three dimensional conformation. Thus, botulinum toxins may be detoxified by heat, various chemicals, surface stretching and surface drying. Additionally, it is known that the dilute toxin concentrations used in the approved indications result in rapid detoxification of the toxin unless a suitable stabilizing agent is present. Moreover, toxin stability is a significant factor on storage. Consequently, stabilizing agents are essential. To date, stability has been achieved through formulation in mammalian derived proteins albumin and gelatin. As noted above, mammalian derived proteins raise the risk that certain stable viruses, prions or other infectious or pathogenic compounds carried through from donors may contaminate the toxin.

Furthermore, the conditions on lyophilization, including pH, temperature, dilution and vacuum pressures operate to detoxify the toxin. To date, mammalian derived proteins such as gelatin and serum albumin have been used with some success to stabilize botulinum toxin and are the standard stabilizers.

For example, the commercially available botulinum toxin containing pharmaceutical composition BOTOX® (available from Allergan, Inc., of Irvine, Calif.) consists of a purified botulinum toxin type A complex, albumin and sodium chloride packaged in sterile, vacuum-dried form. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

The art is replete with attempts to stabilize protein compositions. Carpender et al., Interactions of Stabilizing Additives with Proteins During Freeze-Thawing and Freeze-Drying, International Symposium on Biological Product Freeze-Drying and Formulation, 24-26 Oct. 1990; Karger (1992), 225-239.

The use of the disaccharide cellobiose as an excipient in conjunction with albumin and sodium chloride demonstrates toxicity degradation (10% recovery) after lyophilization of crystalline botulinum toxin type A with these excipients, as compared to the toxicity after lyophilization with only albumin (>75% to >90% recovery). Goodnough et al., Stabilization of Botulinum Toxin Type A During Lyophilization, App & Envir. Micro. 58 (10) 3426-3428 (1992).

Moreover, protein formulations comprising a saccharide (such as glucose or a polymer of glucose) or carbohydrates are not known to be stable because proteins and glucose have been demonstrated to interact together and to undergo Maillard degradation, due to the reducing nature of glucose and glucose polymers. In contrast, alcohols, e.g., inositol, mannitol, are non-reducing and have long been employed as cryoprotectant excipients to stabilize proteins during lyophilization.

In light of the instability of botulinum toxin and the attendant risks of mammalian derived stabilizers and polysaccharides, a suitable protein stabilizer continues to be an objective for formulation scientists.

SUMMARY

It is an object of the present invention to provide a non-proteinaceous replacement for mammalian derived proteins in pharmaceutical compositions containing botulinum toxin or a toxin which is derived from botulinum toxin by chemical modification or by genetic manipulation. This new formulation must have low, and preferably negligible, immunogenicity when injected into a human patient.

DEFINITIONS

As used herein, the words or terms set forth below have the following definitions.

"Pharmaceutical composition" is a formulation in which an active ingredient, in this case a botulinum toxin, or the instant hemagglutinin protein free botulinum toxin, or a toxin which is derived from botulinum toxin by chemical modification or by genetic manipulation, is stabilized by a substance other than a mammalian derived protein. Such pharmaceutical composition may be suitable for diagnostic or therapeutic administration (i.e. by intramuscular or subcutaneous injection) to a human patient. The pharmaceutical composition may be lyophilized or vacuum dried, reconstituted, or in solution. The botulinum toxin active ingredient may be one of the botulinum toxin serotypes A, B, C1, D, E, F or G, all of which may be further modified to be free of the complexing proteins present in natural neurotoxin or modified chemically or modified by genetic manipulation.

"Therapeutic formulation" refers to the capacity of the instant formulation to treat/alleviate a condition such as a condition incident to hyperactivity (i.e. spasticity) of a peripheral muscle.

"Stabilizing", stabilizes" or "stabilization" means that the active ingredient, i.e., a botulinum toxin or a toxin which is derived from botulinum toxin by chemical modification or by genetic manipulation present in a reconstituted or aqueous solution pharmaceutical composition has greater than about 20% and up to about 100% of the toxicity that the biologically active botulinum toxin had prior to being incorporated into the pharmaceutical composition.

"Cryoprotectant" refers to excipients which result in the active ingredient, i.e., a botulinum toxin or a toxin which is derived from botulinum toxin by chemical modification or by genetic manipulation present in a reconstituted or aqueous solution pharmaceutical composition having greater than about 20% and up to about 100% of the toxicity that the biologically active botulinum toxin had prior to being freeze-dried in the pharmaceutical composition.

"pH buffer" refers to chemical substances being capable to adjust the pH value of a composition, solution and the like to a certain value or to a certain pH range.

"Polyalcohol" refers to aliphatic or cycloaliphatic carbohydrates bearing more than one hydroxyl functional group but no carbonyl functional group (like, for instance, in sugar compounds).

"Free from mammalian derived protein stabilizing agents" means that the composition or preparation does not contain detectable amounts of stabilizing agents derived from mammalian proteins.

"Chemical modification" refers to methods known in the art for modifying the native botulinum toxin of any serotype by means of chemical reactions or the like; it refers especially to substitutions, deletions, insertions, additions or posttranslational modifications of amino acids of the botulinum toxin.

"Genetic manipulation" refers to methods known in the art for modifying the native botulinum toxin of any serotype by means of modifying the gene encoding for the botulinum toxin or respective nucleic acids like DNA or RNA.

DESCRIPTION

The present invention describes the discovery that a stable neurotoxin containing pharmaceutical composition may be formulated free of any mammalian derived protein or donor pool albumin by incorporating a non-proteinaceous stabilizing agent, especially by incorporating hyaluronic acid or polyvinylpyrrolidone or polyethyleneglycol or a mixture of two or more thereof. The instant invention pertains to the development of a botulinum toxin composition which is formulated with a hyaluronic acid or polyvinylpyrrolidone or polyethyleneglycol or a mixture of two or more thereof. Such composition is a safer composition possessing remarkable stability.

Fortunately, the instant composition is significant in that the botulinum toxin or a toxin which is derived from botulinum toxin by chemical modification or by genetic manipulation is not formulated in a mammalian derived proteinaceous stabilizer. It has been determined that a hyaluronic acid or polyvinylpyrrolidone or polyethyleneglycol formulation or mixtures thereof, particularly those incorporating a pH buffer, especially sodium acetate buffer, and/or a cryoprotectant, may function to increase the stability and useful storage life of the instant pharmaceutical composition.

Furthermore, the instant pharmaceutical composition or preparation preferably is not only free of a mammalian derived proteinaceous stabilizing agent but free of any stabilizing protein.

The instant invention is not limited to pharmaceutical compositions, but also refers to processes for stabilizing botulinum toxin compositions or compositions of a toxin which is derived from botulinum toxin by chemical modification or by genetic manipulation. By incorporating hyaluronic acid or polyvinylpyrrolidone or polyethyleneglycol or mixtures thereof into the composition, the botulinum toxin or the toxin which is derived from botulinum toxin by chemical modification or by genetic manipulation is stabilized. Moreover, stability may be enhanced by incorporating a pH buffer into the pharmaceutical composition, thereby stabilizing pH and contributing to reconstituted toxin shelf life and/or by including a cryoprotectant into the pharmaceutical composition, thereby increasing freeeze-dry stability and shelf life.

It is preferred that the pH buffer in its nature and amount is capable of stabilizing or adjusting the pH of the instant composition or preparation to values in the range of approximately 4 to about 7.5. Suitable pH buffers may be citrate, phosphate and especially acetate buffer systems, in particular sodium acetate buffer systems. Surprisingly, it has been found that if an acetate buffer is used in the instant composition or preparation and said composition or preparation is freeze-dried, the acetate may be removed from the composition or preparation during freeze-drying; after reconstituting or thawing the composition or preparation has an approximately neutral pH (in the range of about 6.5 to about 7.5). This is advantageous when the composition or preparation is administered to a person or patient in need thereof, especially when injected into a muscle, because the then (almost) neutral botulinum toxin composition or preparation causes less pain than a respective composition or preparation having an acidic pH of, for instance, 4.

A detailed embodiment of the present invention may be a pharmaceutical composition suitable for injection into a human patient, which includes a botulinum toxin or a toxin which is derived from botulinum toxin by chemical modification or by genetic manipulation, and a hyaluronic acid or a polyvinylpyrrolidone or a polyethleneglycol, such composition being optionally pH stabilized by a suitable pH buffer, in particular by a sodium acetate buffer, and/or a cryoprotectant polyalcohol.

The pharmaceutical composition is suitable for administration to a human patient to achieve a therapeutic effect, and the neurotoxin may be one of the botulinum toxin serotypes A, B, C1, D, E, F and G, preferably a botulinum toxin which is free of the complexing proteins present in natural neurotoxin or neurotoxin modified chemically or modified by genetic manipulation. The modified neurotoxin is free of the complexing proteins which naturally form complexes with botulinum neurotoxin as well.

The modification of the neurotoxin derived from botulinum neurotoxin due to chemical modifying or genetic manipulation can be located on each part of the neurotoxin protein, for instance on the heavy chain part and/or on the light chain part of the neurotoxin molecule. There might be one modification or more modifications. Preferably, the heavy chain of the neurotoxin protein derived from botulinum neurotoxin comprises one or more modifications which may decrease or increase the affinity of the neurotoxin for binding to nerve cells when compared to the native neurotoxin. Such modified neurotoxin may comprise at least one substitution and/or deletion and/or insertion and/or addition and or post-translational modification of amino acids of the neurotoxin and preferably of the heavy chain of the neurotoxin.

Whether the pharmaceutical composition comprises, beside the neurotoxin active ingredient, only hyaluronic acid or a polyvinylpyrrolidone or a polyethyleneglycol stabilizer, the pharmaceutical composition retains its potency substantially unchanged for six month, one year, two year, three year and/or four year periods when stored at a temperature between about +8° C. and about −20° C. Additionally, the indicated pharmaceutical compositions may have a potency or percent recovery of between about 20% and about 100% upon reconstitution.

A pharmaceutical composition within the scope of the present invention may include a neurotoxin, and a hyaluronic acid. The hyaluronic acid stabilizes the neurotoxin. The pharmaceutical compositions disclosed herein may have a pH of between about 4 and 7.5 when reconstituted or upon injection. The hyaluronic acid in the instant pharmaceutical composition is preferably combined with the instant botulinum toxin in a quantity of 0.1 to 10 mg, especially 1 mg hyaluronic acid per ml in a 200 U/ml botulinum toxin solution. More preferably, the subject solution also contains a 1-100 mM, especially 10 mM sodium acetate buffer.

In another preferred embodiment, the composition may contain a polyalcohol as cryoprotectant. Examples of polyalcohols that might be used include, e.g., inositol, mannitol and other non-reducing alcohols.

It will be understood that the instant composition or preparation does not contain trehalose or maltotriose or related sugar or polyhydroxy compounds which are sometimes used as cryoprotectants.

The polyvinylpyrrolidone in the instant pharmaceutical composition is preferably combined with the instant botulinum toxin in a quantity of 10 to 500 mg, especially 100 mg polyvinylpyrrolidone per ml in a 200 U/ml botulinum toxin solution. More preferably, the subject solution also contains a 1-100 mM, especially 10 mM sodium acetate buffer.

The polyethyleneglycol in the instant pharmaceutical composition is preferably combined with the instant botulinum toxin in a quantity of 10 to 500 mg, especially 100 mg polyethyleneglycol per ml in a 200 U/ml botulinum toxin solution. More preferably, the subject solution also contains a 1-100 mM, especially 10 mM sodium acetate buffer.

Thus, the instant invention encompasses a botulinum toxin formulated in a pharmaceutical composition which contains a hyaluronic acid stabilizer or a polyvinylpyrrolidone stabilizer or a polyethyleneglycol stabilizer. Additionally, the pharmaceutical composition may contain a sodium acetate buffer system and/or an alcoholic cryoprotectant. The following examples are provided by means of illustration only, and are not intended to be limiting.

The instant preparation or pharmaceutical composition is useful for treating a condition for which botulinum neurotoxin therapy or treatment is indicated. In one aspect it may be used for treating cosmetic conditions like wrinkling and pronounced wrinkling. In another aspect it may be used for treating a condition where the condition is selected from blepharospasm, hemifacial spasms, spasmodic torticollis, spasticities, migraine, low back pain, cervical spine disorders, strabismus, hyperhidrosis, hypersalivation, and dystonias. Furthermore, the instant preparation or composition is also used for the manufacturing of a medicament for a condition for which botulinum neurotoxin therapy is indicated, the condition being preferably selected from cosmetic conditions, blepharospasm, hemifacial spasms, spasmodic torticollis, spasticities, migraine, low back pain, cervical spine disorders, strabismus, hyperhidrosis, hypersalivation, and dystonias. Further medical indications treatable with the instant preparation or composition are, among others, benign cramping, essential tremor, mykomia, neurogenic muscle hypertrophy, palantal myoclonus, spinal myoclonus, synkinesis/cranial nerve VII disorders, Duanne's eye-retraction syndrome, nystagmus, therapeutic ptosis for corneal protection, oscillopsia, spasmodic dysphonia, granuloma, puberophonia, posterior glottic stenosis, rebalancing, stutter, TEP failure, essential voice tremor, vocal tics, cricopharyngeus, bruxism, masseter hypertrophy, morbid obesity, achalasia, anal fissure, anismus, intractable hiccups, severe constipation, anorectal pain, gastroparesis, benign anal disorders, esophageal diverticulosis, sphincter of Oddi, crocodile tears, sialocele, sialorrhea, drooling, parotid fistula, Frey's syndrome, ptyalism, detrusor-spincter dyssnergia, overactive bladder, vaginismus, urinary retention, hyperplasia, benigne hyperplasia, tension headache, cervicogenic pain, myofascial pain, apraxia of eyelid opening, synkinesis secondary to facial nerve palsy, stuttering with glottal blocks, body odor, intrinsic rhinitis.

EXAMPLES

The botulinum toxin preparations of the instant invention, and pharmaceutical compositions thereof and method of treating therewith, are demonstrated to possess unique and advantageous properties, rendering the "subject matter as a whole", as claimed herein unobvious. The botulinum toxin preparations and pharmaceutical compositions thereof have exhibited, in standard accepted reliable test procedures, the following valuable properties and characteristics:

Example 1

Botulinum Toxin Preparation

Pure neurotoxin from *Clostridium botulinum* type A is obtained by a process based on the process of DasGupta & Sathyamoorthy. *Clostridium botulinum* type A is cultivated in a 20 l fermenter in a medium consisting of 2% proteose peptone, 1% yeast extract, 1% glucose and 0.05% sodium thioglycolate. After growth for 72 hours, the toxin is precipitated by adding 3 N sulfuric acid (final pH=3.5). The precipitated and centrifuged biomass is extracted with 0.2 M sodium phosphate buffer at pH 6.0.

After removal of the nucleic acids by precipitation with protamine sulfate, the toxin is precipitated by adding ammonium sulfate. The precipitate which has been solubilized and dialyzed against 50 mM sodium phosphate at pH 6.0 is bound to a DEAE-Sephadex® column at the same pH and eluted with 150 mM NaCl. This is followed by a chromatography on a QAE-Sephadex® column which has been equilibrated with a 50 mM Tris/HCl buffer pH 7.9. The toxin is eluted via a NaCl gradient. In the last step, the toxin is chromatographed on SP-Sephadex® at pH 7.0. In this case, the bound toxin is eluted from the column using a NaCl gradient (0-300 mM). The purified toxin is analyzed by SDS-polyacrylamide gel electrophoresis (SDS-PAGE) and exhibits a purity of 95+/− 5%. The biological activity is determined in the mouse LD50 assay: one LD50 unit corresponds to 4.8 pg of protein.

Example 2

Finished Pharmaceutical Composition Containing Hyaluronic Acid

The purified neurotoxin of Example 1 was used to prepare a solution which comprises 200 U botulinum toxin preparation and 1 mg hyaluronic acid per milliliter of distilled water. The solution was dispensed into vials.

Example 3

Finished Pharmaceutical Composition Containing Hyaluronic Acid and Sodium Acetate Buffer The purified neurotoxin of Example 1 was used to prepare a solution which comprises 200 U botulinum toxin preparation and 1 mg hyaluronic acid per milliliter of distilled water, and adjusted to a pH of 4.5, 5.0 and 5.5 by addition of 10 mM sodium acetate buffer. The solution was dispensed into vials.

Example 4

Determination of Botulinum Toxin Formulation Stability

The formulation of Example 2 was prepared and compared against botulinum toxin formulated in Human Serum Albumin (HSA). On formulation, both preparations possessed the same activity. At 24 and 48 hours, the stability of the formulation of Example 2 matched that of the HSA preparation, with a loss of less than 5% of the initial activity occurring in both samples.

Example 5

Determination of Botulinum Toxin Formulation Stability Under Varied pH

The formulations of Example 3 were prepared and compared against botulinum toxin formulated in Human Serum Albumin (HSA). On formulation, both the instant preparations at every pH point and the HSA preparation possessed the same activity. The pH 4.5 preparation exhibited a loss of approximately 50% of activity by the sixth day. The pH 5.0 and 5.5 preparations lost all activity by the sixth day.

Example 6

Determination of Botulinum Toxin Formulation Stability Under Varied pH and Lyophilization The formulations of Example 3 were prepared and compared against botulinum toxin formulated in Human Serum Albumin (HSA). On formulation, the instant preparation at pH 4.5 possessed the same activity as the HSA preparation. More importantly, no loss of activity was detected on lyophilization.

Example 7

Finished Pharmaceutical Composition Containing Polyvinylpyrrolidone

The purified neurotoxin of Example 1 was used to prepare a solution which comprises 200 U botulinum toxin preparation and 100 mg polyvinylpyrrolidone per milliliter of distilled water. The solution was dispensed into vials.

Example 8

Finished Pharmaceutical Composition Containing Polyvinylpyrrolidone and Sodium Acetate Buffer The purified neurotoxin of Example 1 was used to prepare a solution which comprises 200 U botulinum toxin preparation and 100 mg polyvinylpyrrolidone per milliliter of distilled water, and adjusted to a pH of 4.5, 5.0 and 5.5 by addition of 10 mM sodium acetate buffer. The solution was dispensed into vials.

Example 8A

Finished Pharmaceutical Composition Containing Polyvinylpyrrolidone, Mannitol and Sodium Acetate Buffer The purified neurotoxin of Example 1 was used to prepare a solution which comprises 200 U botulinum toxin preparation, 100 mg polyvinylpyrrolidone and 20 mg mannitol per milliliter of distilled water, and adjusted to a pH of 4.5, 5.0 and 5.5 by addition of 10 mM sodium acetate buffer. The solution was dispensed into vials.

Example 8B

Finished Pharmaceutical Composition Containing Polyvinylpyrrolidone, Sorbitol and Sodium Acetate Buffer The purified neurotoxin of Example 1 was used to prepare a solution which comprises 200 U botulinum toxin preparation, 100 mg polyvinylpyrrolidone and 20 mg sorbitol per milliliter of distilled water, and adjusted to a pH of 4.5, 5.0 and 5.5 by addition of 10 mM sodium acetate buffer. The solution was dispensed into vials.

Example 9

Determination of Botulinum Toxin Formulation Stability

The formulation of Example 7 was prepared and compared against—botulinum toxin formulated in Human Serum Albumin (HSA). On formulation, both preparations possessed the same activity.

Example 10

Determination of Botulinum Toxin Formulation Stability Under Varied pH

The formulations of Example 8 were prepared and compared against botulinum toxin formulated in Human Serum Albumin (HSA). On formulation, both the instant preparations at every pH point and the HSA preparation possessed the same activity. The pH 4.5 and 5.0 as well as the HSA preparations exhibited no loss of activity by within 24 hours of formulation. The pH 5.5 preparation lost 20% activity compared to the HSA and other preparations within 24 hours.

Example 10A

Determination of Botulinum Toxin Formulation Stability Under Varied pH

The formulations of Example 8A were prepared and compared against botulinum toxin formulated in Human Serum Albumin (HSA). On formulation, both the instant preparations at every pH point and the HSA preparation possessed the same activity. The pH 4.5, 5.0 and 5.5 as well as the HSA preparations exhibited no loss of activity by within 24 hours of formulation.

Example 10B

Determination of Botulinum Toxin Formulation Stability Under Varied pH

The formulations of Example 8B were prepared and compared against botulinum toxin formulated in Human Serum Albumin (HSA). On formulation, both the instant preparations at every pH point and the HSA preparation possessed the same activity. The pH 4.5, 5.0 and 5.5 as well as the HSA preparations exhibited no loss of activity within 24 hours of formulation.

Example 11

Determination of Botulinum Toxin Formulation Stability Under Varied pH and Lyophilization The formulations of Example 8 were prepared and compared against botulinum toxin formulated in Human Serum Albumin (HSA). On formulation, both the instant preparations at every pH point and the HSA preparation possessed the same activity. More importantly, less than 10% loss of activity is detected on lyophilization for all formulations for up to 6 months.

Example 11A

Determination of Botulinum Toxin Formulation Stability Under Varied pH and Lyophilization The formulations of Example 8A were prepared and compared against botulinum toxin formulated in Human Serum Albumin (HSA). On formulation, both the instant preparations at every pH point and the HSA preparation possessed the same activity. More importantly, less than 10% loss of activity is detected on lyophilization for all formulations for up to 6 months.

Example 11B

Determination of Botulinum Toxin Formulation Stability Under Varied pH and Lyophilization The formulations of Example 8B were prepared and compared against botulinum toxin formulated in Human Serum Albumin (HSA). On formulation, both the instant preparations at every pH point and the HSA preparation possessed the same activity. More importantly, less than 10% loss of activity is detected on lyophilization for all formulations for up to 6 months.

Example 12

Finished Pharmaceutical Composition Containing Polyethyleneglycol

The purified neurotoxin of Example 1 was used to prepare a solution which comprises 200 U botulinum toxin preparation and 100 mg polyethyleneglycol per milliliter of distilled water. The solution was dispensed into vials.

Example 12A

Finished Pharmaceutical Composition Containing Polyethyleneglycol and Mannitol

The purified neurotoxin of Example 1 was used to prepare a solution which comprises 200 U botulinum toxin preparation, 100 mg polyethyleneglycol and 20 mg mannitol per milliliter of distilled water. The solution was dispensed into vials.

Example 12B

Finished Pharmaceutical Composition Containing Polyethyleneglycol and Sorbitol

The purified neurotoxin of Example 1 was used to prepare a solution which comprises 200 U botulinum toxin preparation, 100 mg polyethyleneglycol and 20 mg sorbitol per milliliter of distilled water. The solution was dispensed into vials.

Example 13

Determination of Botulinum Toxin Formulation Stability

The formulation of Example 12 was prepared and compared against botulinum toxin formulated in Human Serum Albumin (HSA). On formulation, both preparations possessed the same activity.

Example 14

Determination of Botulinum Toxin Formulation Stability

The formulations of Example 12A and 12B were prepared and compared against botulinum toxin formulated in Human Serum Albumin (HSA). On formulation, both instant preparations and the HSA preparation possessed the same activity. The instant preparations as well as the HSA preparation exhibited less than 20% loss of activity by within 24 hours of formulation.

Example 15

Use of a Botulinum Toxin Pharmaceutical Composition

A 50 year old female seeks treatment for blepharospasm. Between about 10 U and about 20 U of a botulinum toxin preparation of Example 3 containing hyaluronic acid is injected intramuscularly into the patient. Within 1-7 days, the symptoms of blepharospasm are alleviated and alleviation of the symptoms persists for at least from about 2 months to about 6 months.

Example 16

Use of a Botulinum Toxin Pharmaceutical Composition

A 50 year old female seeks treatment for blepharospasm. Between about 10 U and about 20 U of a botulinum toxin preparation of Example 8 containing polyvinylpyrrolidone is injected intramuscularly into the patient. Within 1-7 days, the symptoms of blepharospasm are alleviated and alleviation of the symptoms persists for at least from about 2 months to about 6 months.

Example 17

Use of a Botulinum Toxin Pharmaceutical Composition

A 50 year old female seeks treatment for blepharospasm. Between about 10 U and about 20 U of a botulinum toxin preparation of Example 12, containing polyethyleneglycol is injected intramuscularly into the patient. Within 1-7 days, the symptoms of blepharospasm are alleviated and alleviation of the symptoms persists for at least from about 2 months to about 6 months.

Example 18

Use of a Botulinum Toxin Pharmaceutical Composition

A 50 year old female seeks treatment for blepharospasm. Between about 10 U and about 20 U of a botulinum toxin preparation of Example 12A, containing polyethyleneglycol is injected intramuscularly into the patient. Within 1-7 days, the symptoms of blepharospasm are alleviated and alleviation of the symptoms persists for at least from about 2 months to about 6 months.

Example 19

Use of a Botulinum Toxin Pharmaceutical Composition

A 50 year old female seeks treatment for blepharospasm. Between about 10 U and about 20 U of a botulinum toxin preparation of Example 12B, containing polyethyleneglycol is injected intramuscularly into the patient. Within 1-7 days, the symptoms of blepharospasm are alleviated and alleviation of the symptoms persists for at least from about 2 months to about 6 months.

The invention claimed is:

1. A pharmaceutical composition comprising at least one botulinum neurotoxin selected from *Clostridium botulinum* of types A, B, C1, D, E, F and G, wherein the at least one botulinum neurotoxin is free of hemagglutinins and nontoxic non-hemagglutinating proteins; a non-proteinaceous stabilizing agent which retains the biological activity of the neurotoxin in an aqueous solution selected from hyaluronic acid, polyvinylpyrrolidone, and polyethylene glycol; and, optionally, a pH buffer; wherein the composition is free from any stabilizing protein.

2. The pharmaceutical composition of claim 1, wherein the at least one botulinum neurotoxin is modified chemically or by genetic manipulation.

3. The pharmaceutical composition of claim 1, wherein the pH buffer is sodium acetate.

4. The pharmaceutical composition of claim 1, further comprising a polyalcohol cryoprotectant.

5. The pharmaceutical composition of claim 4, wherein the polyalcohol is selected from the group consisting of inositol, mannitol and sorbitol.

6. The pharmaceutical composition of claim 1 which is in freeze-dried form.

* * * * *